United States Patent
Ziv et al.

(10) Patent No.: US 7,378,079 B2
(45) Date of Patent: May 27, 2008

(54) AGENTS FOR IMAGING AND DIAGNOSTIC METHODS USING THEM

(75) Inventors: Ilan Ziv, Kfar Saba (IL); Anat Shirvan, Herzliya (IL); Sharon Ebner, Raanana (IL)

(73) Assignee: NST Neurosurvival Technologies Ltd., Petah-Tikva (IL)

( * ) Notice: Subject to any disclaimer, the term of this patent is extended or adjusted under 35 U.S.C. 154(b) by 195 days.

(21) Appl. No.: 10/516,616

(22) PCT Filed: Jun. 3, 2003

(86) PCT No.: PCT/IL03/00463

§ 371 (c)(1),
(2), (4) Date: Jun. 10, 2005

(87) PCT Pub. No.: WO03/101948

PCT Pub. Date: Dec. 11, 2003

(65) Prior Publication Data

US 2005/0276750 A1    Dec. 15, 2005

(30) Foreign Application Priority Data

| Jun. 4, 2002 | (IL) | 150016 |
| Nov. 4, 2002 | (IL) | 152631 |
| Nov. 28, 2002 | (IL) | 153183 |

(51) Int. Cl.
*A61K 49/00* (2006.01)

(52) U.S. Cl. ............ 424/9.1; 424/1.11; 424/1.37; 424/1.65; 424/1.81; 424/1.85; 424/1.89; 534/14

(58) Field of Classification Search .......... 424/1.11, 424/1.65, 9.1, 9.2, 9.3, 9.4, 9.5, 9.6, 9.7, 424/9.8, 1.37, 1.81, 1.85, 1.89; 534/7, 10–16

See application file for complete search history.

(56) References Cited

FOREIGN PATENT DOCUMENTS

| EP | 0451 824 A2 | 10/1991 |
| WO | WO 02/46147 A2 | 6/2002 |
| WO | WO 02/074346 A2 | 9/2002 |

OTHER PUBLICATIONS

Golub et al., Science, Oct. 15, 1999, pp. 531-537.*
Wilkinson (Journal of Chromatographic Science, 1978, vol. 16, No. 11, pp. 547-552).*
Chiotellis, E. et al. "Structure-Activity Relationships of Some Technetium-99m Labeled [(Thioethyl)amino] Carboxylates", *J. Med. Chem*, vol. 25 pp. 1370-1374, 1982.
Lazarides, E. et al. "Fluorescent localization of membrane sites in glycerinated chicken skeletal muscle fibers and the relationship of these sites to the protein composition of the Z disc", Proc.Natl. Acad.Sci.USA, vol. 75(8) pp. 3683-3687, 1978.
Bevers, E.M. et al. "Lipid translocation across the plasma membrane of mammalian cells", *Biochimica et Biophysica Acta*, vol. 1439 pp. 317-330, 1999.
Bombeli, T. et al. "Apoptic Vascular Endothelial Cells Become Procoagulant", *Blood*, vol. 89(7) pp. 2429-2442, 1997.
Bratton, D.L. et al. "Appearance of Phosphatidylserine on Apoptotic Cells Requires Calcium-mediated Nonspecific Flip-Flop and is Enhanced by Loss of the Aminophospholipid Translocase", *The Journal of Biological Chemistry*, vol. 272(42) pp. 26159-26165, 1997.
Bursch, W. et al. "Cell death by apoptosis and its protective role against disease", *TiPS*, vol. 13 pp. 245-251, 1992.
Kockx, M.M. et al. "Apoptosis in atherosclerosis: beneficial or detrimental?", *Cardiovascular Research*, vol. 45 pp. 736-746, 2000.
Mallat, Z. et al. "Colocalization of CPP-32 With Apoptotic Cells in Human Atherosclerotic Plaques", *Circulation*, vol. 96 pp. 424-428, 1997.
Martin, S.J. et al. "Early Redistribution of Plasma Membrane Phosphatidylserine is a General Feature of Apoptosis Regardless of the Initiating Stimulus: Inhibition by Overexpression of Bcl-2 and Abl", J. Exp. Med., vol. 182 pp. 1545-1556, 1995.
Sims, P.J. et al. "Unraveling the Mysteries of Phospholipid Scrambling", *Thromb Haemost*, vol. 86 pp. 266-275, 2001.
Stary, H.C. et al. "A Definition of Advanced Types of Atherosclerotic Lesions and a Histological Classification of Atherosclerosis", *Circulation*, vol. 92 pp. 1355-1374, 1995.
Van den Eijnde, S.M. et al. "Phosphatidylserine plasma membrane asymmetry in vivo: a pancellular phenomenon which alters during apoptosis", *Cell Death and Differentiation*, vol. 4 pp. 311-316, 1997.

* cited by examiner

*Primary Examiner*—Dameron L. Jones
(74) *Attorney, Agent, or Firm*—The Nath Law Group; Gary M. Nath; Susanne M. Hopkins

(57) ABSTRACT

The present invention provides novel compounds that bind selectively to cells undergoing perturbations and alterations of the normal organization of their plasma membrane, while binding to a lesser degree to cells having membranes of normal organization, and their uses as diagnostic probes. Said compounds and methods used therein may be useful in medical practice, for applications such as diagnosis of disease and monitoring of response to therapy.

19 Claims, 4 Drawing Sheets

AGENTS FOR IMAGING AND DIAGNOSTIC METHODS USING THEM

This application is a National Phase Application of PCT/IL03/00463, International Filing Date Jun. 3, 2003, which claims the priority of Israeli Patent Applications Nos. IL 150016, filed Jun. 4, 2002; IL 152631, filed Nov. 4, 2002; and IL 153183, filed Nov. 28, 2002, which are incorporated hereto in their entirety by reference.

FIELD OF THE INVENTION

The present invention relates to novel compounds useful as imaging agents, and diagnostic methods using them for detecting a disease process, for monitoring the progression of a disease and/or for monitoring of the effect of treatment.

LIST OF REFERENCES

The following references are considered to be pertinent for the purpose of understanding the background of the present invention:

Bevers, E. M., et al., *Biochim. Biophys. Acta*, 1439:317-330, 1999;
Bombeli, T., et al., *Blood*, 89:2429-2442, 1997;
Bratton, D. L., et al., *J. Biol. Chem.*, 272:26159-26165, 1997;
Bursch, W., et al., *Trends Pharmacol. Sci.*, 13:245-251, 1992;
Kockx M. M., et al., *Cardiovasc. Res.*, 45:736-746, 2000;
Mallat, Z., et al., *Circulation*, 96:424-428, 1997;
Martin, S., et al., *J. Exp. Med.*, 182:1545-1556, 1995;
Sims, P. J., et al., *Thromb. Haemost.*, 86:266-275, 2001;
Stary, H. C., et al., *Circulation*, 92:1355-1374, 1995;
Van den Eijnde, S. M., et al., *Cell Death Diff.*, 4:311-316, 1997.

The above references will be acknowledged in the text below by indicating in brackets, from the above list, the name of the first author and the year of publication.

BACKGROUND OF THE INVENTION

The plasma membrane (outer membrane) of intact eukaryotic cells is characterized by a highly organized structure. This high level of organization is determined, among others, by the molecular structure of the specific lipids constituting the membrane; the ratio between the various lipid species from which the membrane is composed; the distribution of the phospholipids between the outer and inner leaflets of the membrane; and by the membrane protein constituents.

While maintenance of the high level of membrane organization is fundamental to normal cell physiology, substantial perturbations and alterations of the normal organization of the cell plasma membrane (PNOM) occur in numerous physiological and pathological conditions, and are characterizing a plurality of diseases (Martin, S., et al., 1995). Such alterations and perturbations may be evident both at the morphological level (membrane blebbing observed in cells undergoing apoptosis) and at the molecular level. The scope of perturbations accompanying either cell activation, cell disease or cell death is not fully elucidated. They include, among others, scrambling and redistribution of the membrane phospholipids, with movement to the cell surface of aminophsopholipids, mainly phosphatidylserine (PS) and phosphatidylethanolamine (PE), which are normally restricted almost entirely to the inner leaflet of the membrane bilayer, and reciprocal movement of sphingomyelin (SM) and phosphatidylcholine (PC) from the outer leaflet to the inner leaflet of the membrane (Sims, P. J., et al., 2001). This redistribution is referred herein as loss of cell membrane lipid asymmetry (CMLA).

These alterations play an indispensable role in making the cell surface a catalytic platform for the assembly of several clotting factor complexes, such as the tenase and prothrombinase protein complexes (Bevers, E. M., et al., 1999). Thus, platelets undergo PNOM upon activation, and these alterations constitute an important factor in normal blood coagulation, as well as in the initiation and/or propagation of abnormal, excessive blood clotting in numerous disorders. These disorders include, among others, arterial or venous thrombosis or thrombo-embolism [e.g., cerebral stroke, myocardial infarction, deep vein thrombosis (DVT), disseminated intravascular coagulation (DIC), thrombotic thrombocytopenic purpura, etc.]; unstable atherosclerotic plaques, sickle cell disease; beta-thalassemia; anti-phospholipid antibody syndrome; among others in systemic lupus erythematosus (SLE); disorders associated with shedding of membrane microparticles, e.g., neurological dysfunction in association with cardiopulmonary bypass.

Apoptosis is another major situation in which alterations/perturbations of cell membrane take place (Bratton, D. L., et al., 1997). Apoptosis is an intrinsic program of cell self-destruction or "suicide", which is inherent in every eukaryotic cell. In response to a triggering stimulus, cells undergo a highly characteristic cascade of events of cell shrinkage, blebbing of cell membranes, chromatin condensation and fragmentation, culminating in cell conversion to clusters of membrane-bound particles (apoptotic bodies), which are thereafter engulfed by macrophages (Bursch, W., et al., 1992). PNOM is a universal phenomenon in apoptosis, it occurs early in the apoptotic cascade, probably at the point of cell commitment to the death process, and has also been shown to be an important factor in the recognition and removal of apoptotic cells by macrophages (Van den Eijnde, S. M., et al., 1997).

A strong correlation has been recently drawn between PNOM and potent procoagulant activity of apoptotic cells (Bombeli, T., et al., 1997). PNOM in apoptotic endothelial cells, such as in atherosclerotic plaques (Mallat, Z., et al., 1997), probably plays an important role in the pathogenesis of thrombotic vascular disorders. PNOM is also a feature of inflammatory cells (i.e., lymphocytes, macrophages), activated by various triggers.

Since apoptosis, thrombosis or inflammation have an important role in the majority of medical disorders, it is desirable to have tools for detection of these biological processes. Compounds for selective binding to PNOM membranes, potentially also performing subsequent entry into these cells having such PNOM membranes, may therefore serve as an important tool for detecting and targeting of cells undergoing damage or death process, especially by apoptosis, or undergoing activation. In the clinical context, detection of binding to said membranes may be useful in the diagnosis of disease, in monitoring course or progression of a disease, or in monitoring the effect of various therapeutic approaches utilized to alter disease course.

SUMMARY OF THE INVENTION

The present invention provides new compounds. The new compounds of the invention are useful as imaging agents for detecting a disease process, for monitoring the progression of a disease process, and/or for monitoring of the 10 results of therapy.

According to one aspect, the present invention provides new sulfonamide derivatives, having the following formula

I:

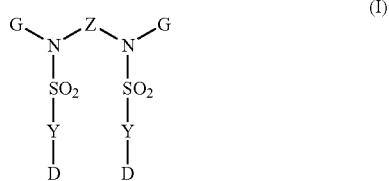

including pharmaceutically acceptable salts, metal chelates, solvates and hydrates of the structure of formula (I); wherein Y groups may be the same or different at each occurrence, each being selected from a bicyclic aromatic or heteroaromatic system of 8, 9 or 10 atoms in the cyclic nucleus; said aromatic or heteroaromatic system optionally being substituted by at least one of a halogen (said halogen being —Br, —Cl, —I, or —F) or a —NO$_2$ group and wherein said heteroaromatic system comprises at least one heteroatom selected among N, O and S;

G groups may be the same or different at each occurrence, and are selected independently among hydrogen, —(CH$_2$)$_m$CH(NH$_2$)(COOH), —(CH$_2$)$_m$COOH; m being an integer selected from 0,1,2,3 and 4;

D is WR$_b$, wherein W is selected among null, N, C and O;

R represents hydrogen, linear or branched alkyl of 1, 2, 3 or 4 carbon atoms, or the group (CH$_2$)$_m$CH(NH$_2$)COOH, wherein m is an integer of 0, 1, 2, 3 or 4; R moieties may be either the same or different; and in the case that W is an oxygen atom b is 1
in the case that W is a nitrogen atom b is 1 or 2;
and in the case that W is a carbon atom b is 3;

Z is a group having the formula —U(G)(M)-T—U(G)(M)-;

wherein G groups may have the same meanings as above at each occurrence;

M groups may be the same or different, and are each independently selected from null, hydrogen, alkyl-amide (the term alkyl-amide being interchangeably used with the term acylamine), hydroxyalkyl and fluoroalkyl, wherein said alkyl having 1, 2 or 3 carbon atoms.

U groups may be the same or different, and are each independently selected from null or an optionally substituted, linear or branched alkylene of 1, 2, 3 or 4 carbon atoms;

T is selected from —O—, —S—, —NH—, —N(B)-,-Q-, —N(B'-Q)—, —N(B'—OH)—, -and —N(B'—F)—;

wherein B is an optionally substituted alkyl of 1, 2, 3, 4, 5 or 6 carbon atoms and B' is an optionally substituted alkylene of 1, 2, 3, 4, 5 or 6 carbon atoms;

Q is selected from a marker for imaging and a metal chelate; said marker for imaging being selected from the group comprising a fluorescent label, a radio-label, a marker for X-ray, a marker for MRI, a marker for PET scan and a label capable of undergoing an enzymatic reaction that produces a detectable color.

In a preferred embodiment, Q is a metal chelate comprising Technetium, oxo-Technetium, Gallium, Rhenium, oxo-Rhenium, Indium isotopes, Gadolinium, iron or manganese ions.

In another preferred embodiment Q is selected from $^{18}$F and $^{124}$I. In such case, Q may also be linked directly to either the Y or the D moieties.

In yet another preferred embodiment the Y group is substituted by $^{18}$F.

In the case that Q is a chelate, the chelator therein preferably comprises nitrogen, and/or sulfur, and/or oxygen atoms, participating in the metal chelation. In such preferred embodiment, metal chelation is accomplished through a combination of atoms selected from three nitrogen atoms and one sulfur atom (hereinafter referred to as N$_3$S metal chelators); two nitrogen atoms and two sulfur atoms (hereinafter referred to as N$_2$S$_2$ metal chelators); one nitrogen atom and three sulfur atoms (hereinafter referred to as NS$_3$ metal chelators), or oxygen atoms. Examples of such metal chelators are chelators comprising diaminedithiols, monoamine-monoamide-bisthiols (MAMA), triamide-monothiols, and monoamine-diamide-monothiols. In another preferred embodiment, metal chelation is accomplished through oxygen atoms. Examples of such metal chelators are diethylenetriaminepentaacetate (DTPA), and tetraazacyclododecanetetraacidic acid (DOTA).

In a preferred embodiment the compounds of the present invention have the following formula II:

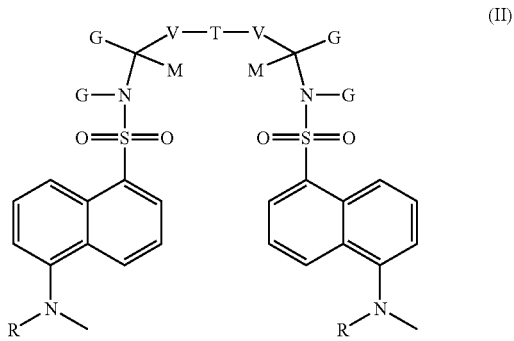

including pharmaceutically acceptable salts, hydrates, solvates and metal chelates of the compound of the formula II, wherein G groups may be the same or different and are selected independently among hydrogen, —(CH$_2$)$_m$(COOH) and COOH wherein m is an integer of 1, 2 or 3; V groups may be the same or different and are selected among null or —(CH$_2$)$_k$—; k being 1 or 2;

and T, M and R are as defined above.

Advantageously the compounds of the invention have the following formula III:

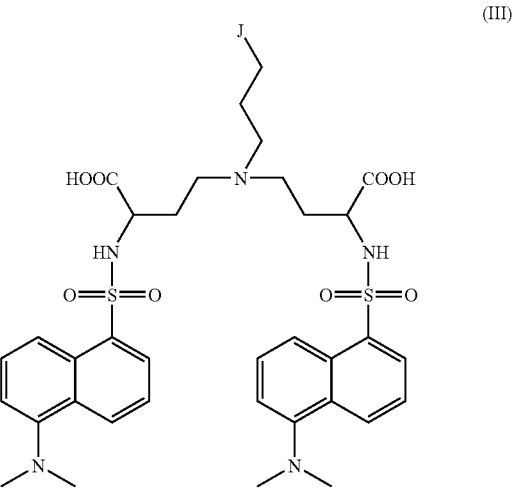

including pharmaceutically acceptable salts hydrates, solvates and metal chelates of the compound of the formula III, wherein J is selected among hydrogen, —OH, and -Q; wherein said Q is selected among an $N_2S_2$ chelator and —F.

In the case that J is —OH the compound is designated NST912 and has the following formula IV:

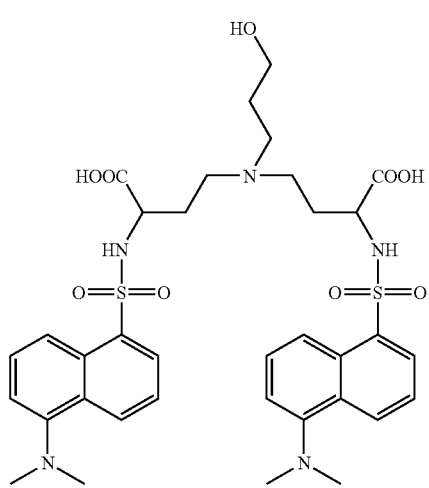

(IV)

including pharmaceutically acceptable salts and hydrates, solvates and metal chelates of the compound of the formula IV.

In the case that J is F the compound is designated NST913 and has the following formula V:

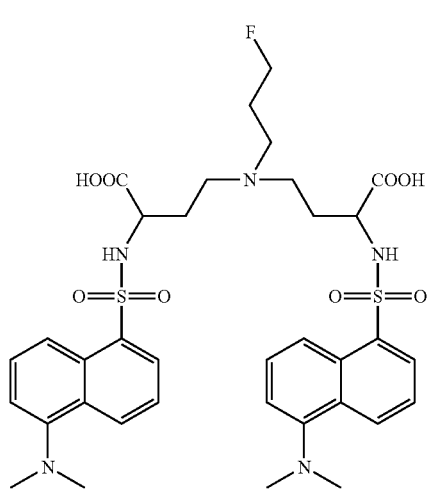

(V)

including pharmaceutically acceptable salts and hydrates, solvates and metal chelates of the compound of the formula V.

In another preferred embodiment the compound of the invention has the following formula VI and is designated NST920B:

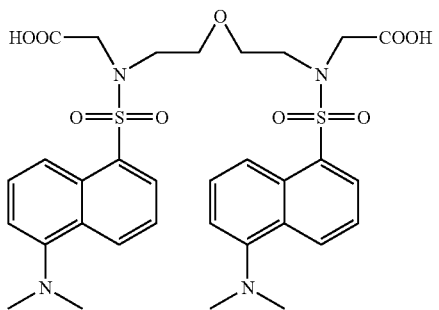

(VI)

including pharmaceutically acceptable salts and hydrates, solvates and metal chelates of the compound of the formula VI.

In another preferred embodiment, the compounds of the invention have the following formula VII:

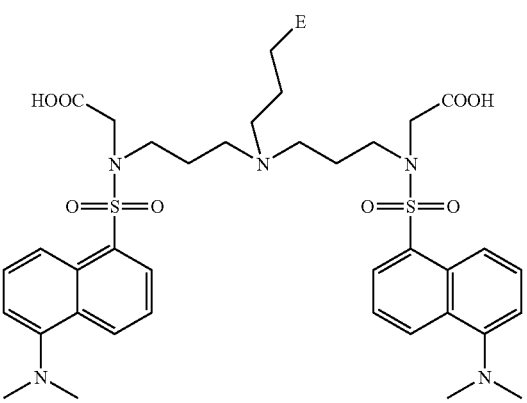

(VII)

including pharmaceutically acceptable salts, hydrates, solvates and metal chelates of the compound of the formula VII.

wherein E is selected from —OH, —F, —CH$_3$ and Q; wherein said Q is an $N_2S_2$ chelator.

In the case that E is —CH$_3$ the compound is designated NST920A and has the following formula VIII:

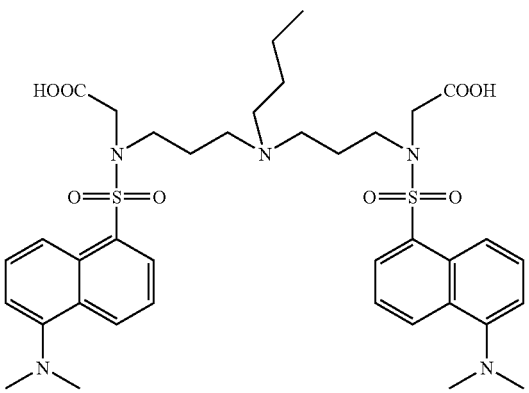

(VIII)

including pharmaceutically acceptable salts, hydrates, solvates and metal chelates of the compound of the formula VIII.

In the case that E is F the compound is designated NST930 and has the following formula IX:

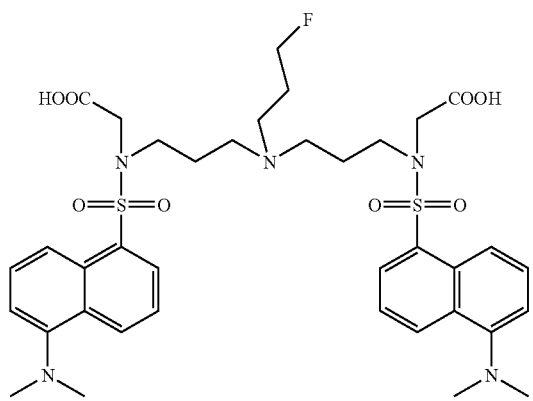

(IX)

including pharmaceutically acceptable salts, hydrates, solvates and metal chelates of the compound of the formula IX.

In another specific embodiment the compound of the invention has the following formula X, and is designated NST850:

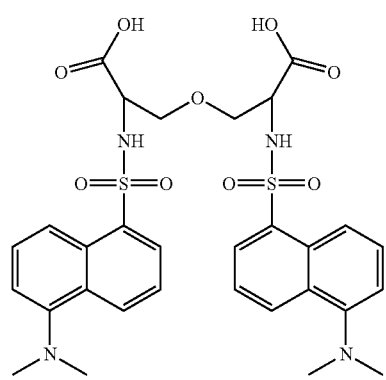

(X)

including pharmaceutically acceptable salts, hydrates, solvates and metal chelates of the compound of the formula X.

In yet another specific embodiment the compound of the invention has the following formula XI, and is designated NST851:

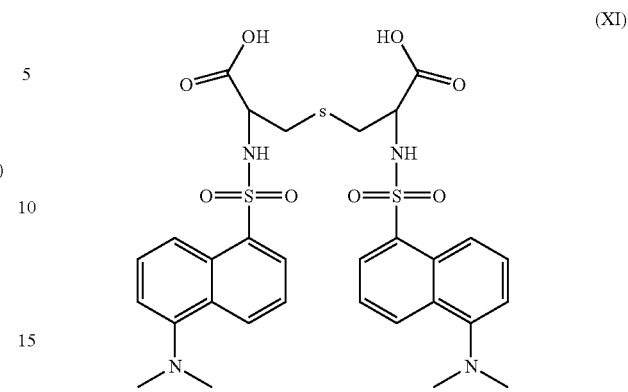

(XI)

including pharmaceutically acceptable salts, hydrates, solvates and metal chelates of the compound of the formula XI.

In yet another specific embodiment, the compound of the invention has the following formula XII, and is designated NST 904:

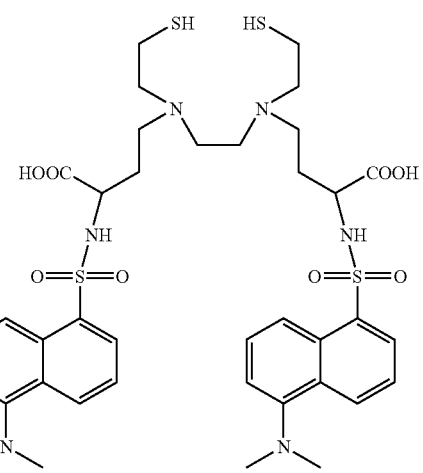

(XII)

including pharmaceutically acceptable salts, hydrates, solvates and metal chelates of the compound of the formula XII. Preferably, said metal chelates are Technetium or Rhenium or oxo-rhenium or oxo-technetium chelates.

One desired property of the compounds of the present invention, is the selective binding of said compounds to membranes of cells, undergoing perturbation of their normal plasma membrane organization (PNOM), with potential subsequent entry into and accumulation within said cells; while essentially binding/accumulating substantially less within cells maintaining their normal membrane organization. This property may be useful for the detection of cells or cell-derived particles, which contain PNOM membranes (PM), said cells being is designated "PM cells", and said detection being designated the "detection aspect" of the invention.

The term PNOM for the purpose of the present invention refers to a cell membrane featuring at least one of the following:

(i) Scrambling of membrane phospholipids, with reduction of normal asymmetry of distribution of phospholipids between the inner and outer leaflets of the plasma membrane;

(ii) Exposure of aminophospholipids on the outer cell surface (mainly exposure of phosphatidylserine and phosphatidylethanolamine);

(iii) Impairment of packing of membrane constituents;

(iv) Impairment of normal distribution of lipids within each membrane leaflet, such as formation of lateral domains, being either enriched or poor in a specific lipid membrane constituent, e.g., phosphatidylserine or cholesterol, respectively.

Therefore, the compounds of the invention may be used for the diagnosis of medical disorders in which cells undergo PNOM, as will be explained herein below.

Thus, according to another of its aspects, the present invention provides a novel diagnostic agent, comprising a compound of formula I as defined above, and a marker for imaging, said marker being the source of a signal detectable by one or more imaging techniques [e.g., radio-isotope scan, magnetic resonance imaging (MRI)].

In a preferred embodiment, Q is a metal chelate, and said marker for imaging is a metal atom, chelated within said Q moiety.

According to another aspect, the diagnostic agent is a compound of the Formula I as defined above, wherein Q is a radioisotope of a material other than a metal, said radioisotope being the source of a signal detectable by imaging technique.

Optionally, the diagnostic agent is a compound of the Formula I as defined above, having fluorescent properties that may be detected by fluorescence techniques (e.g. a fluorescent microscope).

In another aspect thereof, the present invention provides a diagnostic composition comprising an active component that is a compound of the invention of the formula I, that has detectable properties of its own or is capable of chelating a detectable label such as a metal, together with a biologically acceptable carrier, for the detection of PM cells, in a sample of biological cells, in vitro, ex vivo, in vivo or for clinical imaging. The active compound of the present invention is capable of selectively binding/entering PM cells present in the assayed sample. Subsequently, said binding may be identified by any means known in the art.

According to another aspect, the present invention provides a diagnostic kit for the administration of a diagnostic composition or a diagnostic agent to a subject in order to diagnose a physiological disorder. Such diagnostic kit comprises one or more vials containing a sterile formulation comprised of a predetermined amount of lo a diagnostic composition or diagnostic agent of the invention and optionally other components, such as stabilization aids, solubilization aids or bacteriostats. The one or more vials that contain all or part of the formulation can independently be in the form of a sterile solution or a lyophilized solid.

In a preferred embodiment, the diagnostic composition is a diagnostic radio-composition, for radio-imaging by standard radio-imaging techniques, such as single photon emission computed tomography (SPECT), the metal being a radioisotope of the following metal atoms: Tc, In, Cu, Ga, Xe, Tl and Re, preferably Tc, Tc=O, Re and Re=O; or the covalently linked radiolabel, such as $^{123}$I and $^{131}$I. For example, a preferred embodiment is a compound of the invention, radiolabeled with $^{99m}$Tc=O, for detection by SPECT.

In another preferred embodiment, the diagnostic composition is a diagnostic radio-composition for Positron Emission Tomography (PET) scan, comprising a covalently linked radiolabel (the Q moiety), selected from the group $^{18}$F, $^{15}$O, $^{18}$O, $^{11}$C, $^{13}$C, $^{124}$I, $^{13}$N and $^{75}$Br.

In yet another preferred embodiment, the diagnostic composition is a MRI contrast composition, the metal being a paramagnetic metal ion selected from: Gd(III), Fe(III) or Mn(II).

In yet another preferred embodiment, the diagnostic composition is an X-ray or computerized tomography (CT) contrast composition, comprising a contrast agent such as Ba, Cs, Re, Rh, Ag, Ir or iodine.

The term "disease characterized by PM" refers to a disease of which one of its manifestations is PM cells, occurring in tissues inflicted by the disease. This is not meant to indicate that this perturbation of normal cell membrane structure of these cells is necessarily the cause, or the sole effect of the disease, but rather that it is one of its manifestations.

The compounds and the diagnostic agents of the invention can be used for a detection of the following conditions:

1) apoptotic cells and apoptotic bodies;
2) damaged cells and cells undergoing non-apoptotic modes of cell death;
3) activated platelets;
4) activated inflammatory cells, such as activated white blood cells or tissue macrophages.

Therefore, the compounds and the agents of the invention can be useful in the diagnosis of a wide variety of biological conditions, in which the above cells and cell-derived particles have a role. These include physiological conditions such as tissue development or aging, and also various pathological conditions.

According to the detection aspect of the invention, the compounds of the invention may be used, among others, for any of the following three major classes of indications:

(i). Diagnosis of medical disorders in which cells undergo PNOM;

(ii). Monitoring the progression of said medical disorders;

(iii). Monitoring the effects of treatments administered to patients suffering from said diseases.

Examples of such medical disorders are as follows:

Diseases which are characterized by occurrence of excessive apoptosis, such as degenerative disorders, neurodegenerative disorders (e.g., Parkinson's disease, Alzheimer's disease, Huntington chorea), AIDS, myelodysplastic syndromes, ischemic or toxic insults, graft cell loss during transplant rejection; tumors, and especially highly malignant/aggressive tumors, are also often characterized, in addition to the excessive tissue proliferation, also by occurrence of enhanced apoptosis within the tumor tissue.

Diseases manifested by excessive blood clotting, wherein PNOM occur during platelet activation, and/or during activation of or damage to other cellular elements (e.g., endothelial cells). These diseases include, among others, arterial or venous thrombosis, thrombo-embolism, e.g., myocardial infarction, cerebral stroke, deep vein thrombosis, disseminated intravascular coagulation (DIC), thrombotic thrombocytopenic purpura (TTP), sickle cell diseases, thalassemia, antiphospholipid antibody syndrome, systemic lupus erythematosus.

Inflammatory disorders, and/or diseases associated with immune-mediated etiology or pathogenesis, such as autoimmune disorders such as antiphospholipid antibody syndrome, systemic lupus erythematosus, connective tissue disorders such as rheumatoid arthritis, scleroderma; thyroiditis; dermatological disorders such as pemphigus or erythema nodosum; autoimmune hematological disorders; autoimmune neurological disorders such as myasthenia gravis; multiple sclerosis; inflammatory bowel disorders such as ulcerative colitis; vasculitis.

Athlerosclerotic plaques, and especially plaques that are unstable, vulnerable and prone to rupture, are also characterized by PM cells, selected from apoptotic macrophages, apoptotic smooth muscle cells, apoptotic endothelial cells, activated platelets and activated inflammatory cells.

The detection of these pathological conditions, disorders or diseases via detection of the PM cells may be an aim by itself, simply for diagnosis of the presence of a disease condition in a specific individual. The detection may be carried out under in-vivo or in-vitro conditions.

As mentioned above, said detection may also be carried out in a person already known to have the disease, for the purpose of evaluating the disease severity and/or in order to monitor response to various therapeutic modalities. An example for such monitoring is evaluation of response to anticancer therapy. Since most anti-tumor treatments, chemotherapy or radiotherapy exert their effect by induction of cell death, and particularly apoptosis, detection by the agents of the invention of therapy-induced apoptosis of tumor cells may substantially assist in the proper evaluation of the efficacy of said treatments.

Moreover, said detection may be used to monitor adverse effects of anti-cancer treatments. A large part of such adverse effects are due to untoward treatment-induced apoptosis of normal, yet sensitive cells, such as various types of epithelial cells or cells of the bone marrow hematopoietic system. Detection by the compounds of the invention of such apoptosis may allow early detection of this untoward tissue damage and better optimization of the treatment protocol.

In addition, said detection may aim at characterization of an intrinsic apoptotic load within a tumor, i.e., naturally-occurring apoptosis within a tumor. Said characterization may be useful in the assessment of the level of tumor aggressiveness, and may also assist in detection of metastases.

Similarly, the compounds of the current invention may be useful in monitoring graft survival after organ transplantation, since apoptosis, potentially detectable by the compounds of the invention, plays a major role in cell loss during graft rejection. Early diagnosis of such rejection is of major clinical importance, and is currently being achieved mainly by recurrent invasive and potentially life-risking tissue biopsies. The method of the invention may be useful as a non-invasive method for imaging of cell death within the graft, and thus may provide a useful information on the level of graft rejection while saving said biopsies.

In addition, said detection may be useful for monitoring response to cyto-protective agents, administered to inhibit cell death in disorders such as degenerative disorders or various ischemic and toxic insults. Thus the compounds and method of the present invention may aid in the screening and development of drugs capable of inhibiting cell loss in various diseases (for example those recited above) by enabling a measure of evaluation of cell death.

The detection aspect of the invention may also be useful for detection of atherosclerotic plaques (Kockx M. M., et al., 2000; Stary, H. C., et al., 1995), since the destabilization of such plaques, rendering them vulnerable, prone to rupture, thrombosis and embolization, is characterized by participation of several types of PM cells, such as:
  (i). apoptotic cells: the unstable plaque is characterized by apoptotic macrophages, apoptotic smooth muscle cells, and apoptotic endothelial cells
  (ii). activated platelets
  (iii). activated inflammatory cells.

The detection may also take place for basic research purposes, in the study of apoptosis in tissue culture and animal models. Said detection may help in determining the role of apoptosis not only is disease states, but also in normal development and homeostasis of various tissues, such as in the development of the central nervous system during embryogenesis, as well as in situations such as normal aging.

In accordance with this approach, the present invention further concerns a method for the detection of PM cells, the method comprising:
  (i) contacting a sample of cells with a diagnostic agent of the invention under conditions enabling binding/accumulation of said agent in cells;
  (ii) detecting the diagnostic agent in said cells; the presence of a significant amount of the agent in cells indicating the presence of PNOM in said cells.

The method of the present invention may be used for the diagnosis of a disease characterized by the occurrence of PNOM, for example, any one of the diseases indicated above.

The method of the present invention may also be used for monitoring the effects of various therapeutic modalities for said diseases or medical conditions, or alternatively for basic science research purposes as explained above.

The composition of the invention may be administered by any of the known routes, inter alia, oral, intravenous, intraperitoneal, intramuscular, subcutaneous, sublingual, intragastric, intraocular, intranasal or topical administration. The carrier should be selected in accordance with the desired mode of administration, and include any known components, e.g. solvents; emulgators, excipients, talc; flavors; colors, etc. The pharmaceutical composition may also comprise, if desired, also other pharmaceutically-active compounds which are used to treat disease, eliminate side effects or augment the activity of the active component.

The present invention further provides a novel method for the detection of physiological disorders characterized by the presence of PM cells, and/or diseases in which PM cells have an etiological or a pathogenetic role, such method comprising:
  (1) administering a diagnostic composition of the present invention to a patient; and
  (2) imaging of the patient using an appropriate imaging technique, known to those of art.

In a preferred embodiment, the present invention provides a novel method for the detection of physiological disorders characterized by the presence of PM cells, and/or diseases in which PM cells have an etiological or a pathogenetic role, such method comprising:
  (1) administering a radio-composition of the invention to a patient; and
  (2) imaging of the patient using radio-imaging techniques known to those of the art, such as single photon emission tomography (SPECT) in the case of a radio-composition comprising $^{99m}$Tc, or positron emission tomography (PET) in the case of a radio-composition comprising $^{18}$F.

In another preferred embodiment, the present invention provides a novel method for the detection of physiological disorders characterized by the presence of PM cells, and/or diseases in which PM cells have an etiological or a pathogenetic role, such method comprising:
  (1) administering a MRI contrast composition of the invention to a patient; and
  (2) imaging the patient using magnetic resonance imaging techniques, known to those of the art.

In yet another preferred embodiment, the present invention provides a novel method for the detection of physiological disorders characterized by the presence of PM cells, and/or diseases in which PM cells have an etiological or a pathogenetic role, such method comprising:
(1) administering a X-ray contrast composition of the present invention to a patient; and
(2) imaging the patient using X-ray or computed tomography (CT) techniques, known to those of the art.

In yet another preferred embodiment, the present invention provides a novel method for the detection of physiological disorders characterized by the presence of PM cells, and/or diseases in which PM cells have an etiological or a pathogenetic role, such method comprising:
(1) administering a composition of the present invention to a patient;
 wherein the diagnostic agent is a fluorescence-emitting moiety; and
(2) imaging the patient using fluorescence techniques known to those of the art (e.g. a fluorescent microscope).

BRIEF DESCRIPTION OF THE DRAWINGS

In order to understand the invention and to see how it may be carried-out in practice, preferred embodiments will now be described, in which the selective binding/accumulation of the compounds of the present invention in PM cells is demonstrated. PNOM was induced in said cells by induction of apoptosis, and detection of said compounds was performed by monitoring of their intrinsic fluorescence, either by fluorescent microscopy or by flow-cytometric analysis (FACS). Said preferred embodiments will now be described by way of non-limiting example only, with reference to the accompanying drawings, in which.

DETAILED EXPLANATION OF FIGURES

Figure 1:
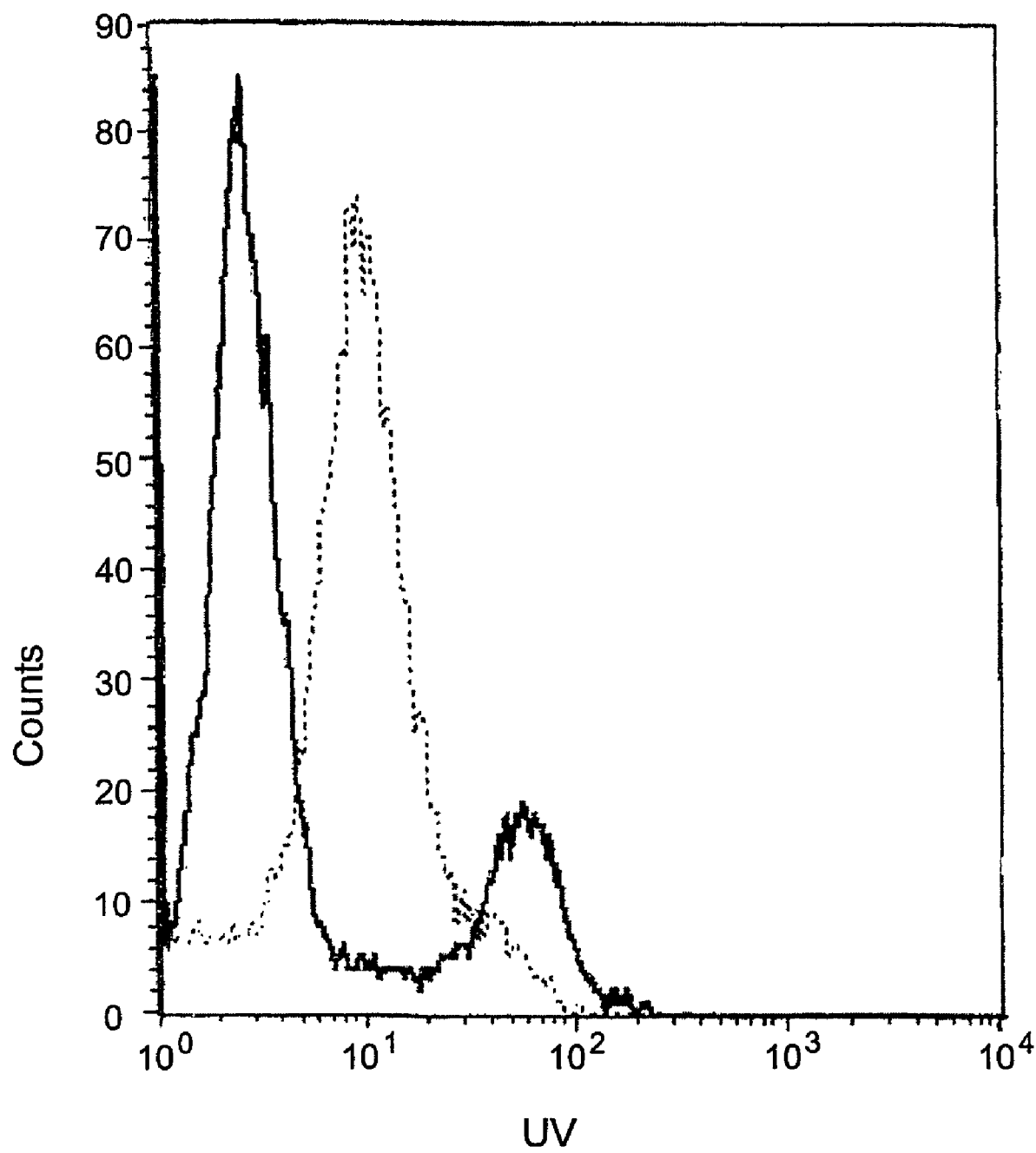
FIG. 1: flow-cytometric analysis demonstrating the selective binding of NST912 to Jurkat cells in the early stages of apoptosis induced by anti-Fas antibody.

FIG. 1: Flow-Cytometric Analysis Demonstrating the Selective Binding of NST912 to Apoptotic Jurkat Cells:

Jurkat cells were induced to undergo apoptosis by exposure to 0.1 µg/ml anti-Fas antibody for 2 hours. Non-treated cells served as control. Cells were then incubated with NST912 (50 µM for 30 min., and subjected to flow-cytometric FACS analysis, using a Becton-Dickinson cell sorter and a CellQuest software. Excitation was at 356 nm and emission was at 530 nm.

Control, non-treated cells exhibit a major peak of low fluorescence (FIG. 1, solid line). The smaller peak at higher fluorescence value represents the population of cells in late apoptosis, naturally-occurring within all cultures. Induction of apoptosis was associated with a shift of the cell population and emergence of a novel peak of higher fluorescence intensity (FIG. 1; dotted line). It reflects selective binding and accumulation of NST912 by these cells in early apoptosis. The X-axis represents the fluorescence in 530 nm, and the Y axis represents the number of cells.

Figure 2:
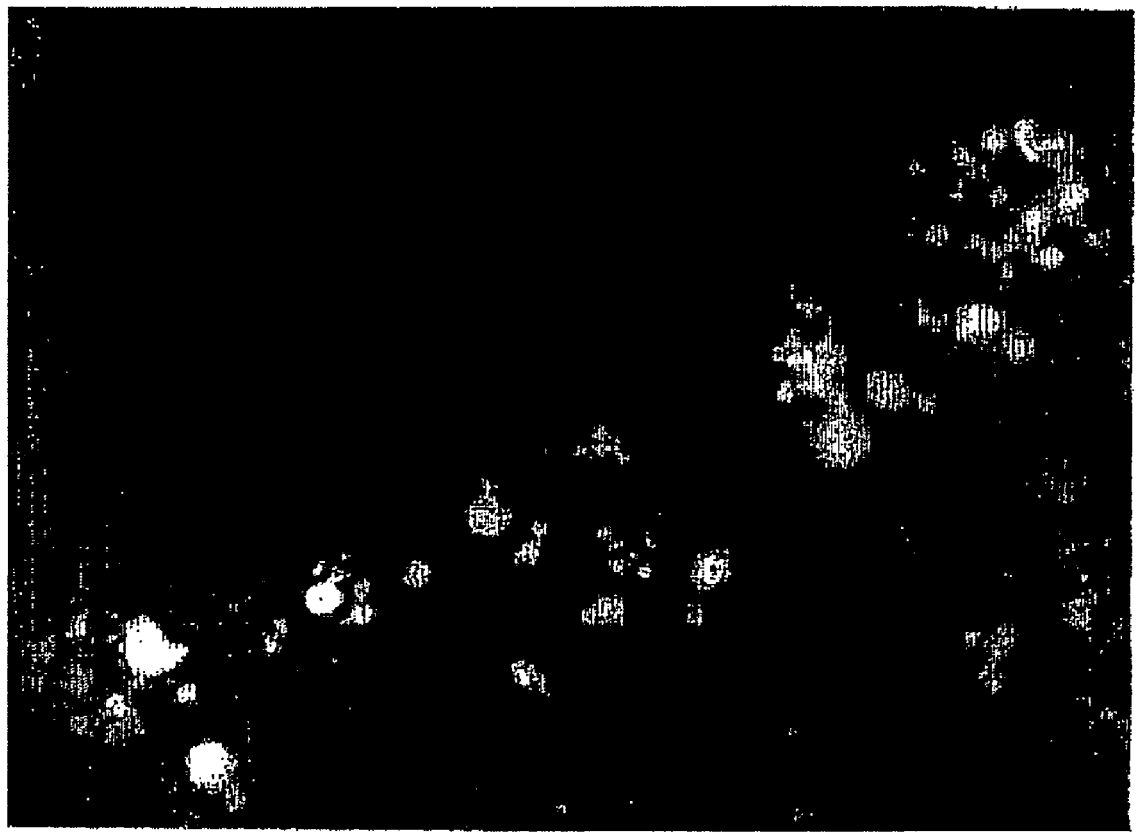
FIG. 2: detection of apoptosis of small intestine epithelial cells, induced in mice by systemic administration of chemotherapy; said detection being performed by NST912 in vivo.

FIG. 2: Detection of Chemotherapy-Induced Apoptosis of Small Intestine Epithelial Cells In Vivo by NST912:

Balb/c mice were treated with a single dose of chemotherapy [Taxol (27 mg/kg)+cyclophosphamide (300 mg/kg)]. Twenty-four hours later, the animals were injected intravenously with NST912. Animals were sacrificed two hours later, and the small intestine tissue was removed and subjected to fluorescent histopathological analysis. Numerous cells within the intestinal crypta undergoing apoptosis demonstrated selective uptake and accumulation of NST912. No such staining was observed in the small intestine of control animals, not receiving chemotherapy.

Figure 3:
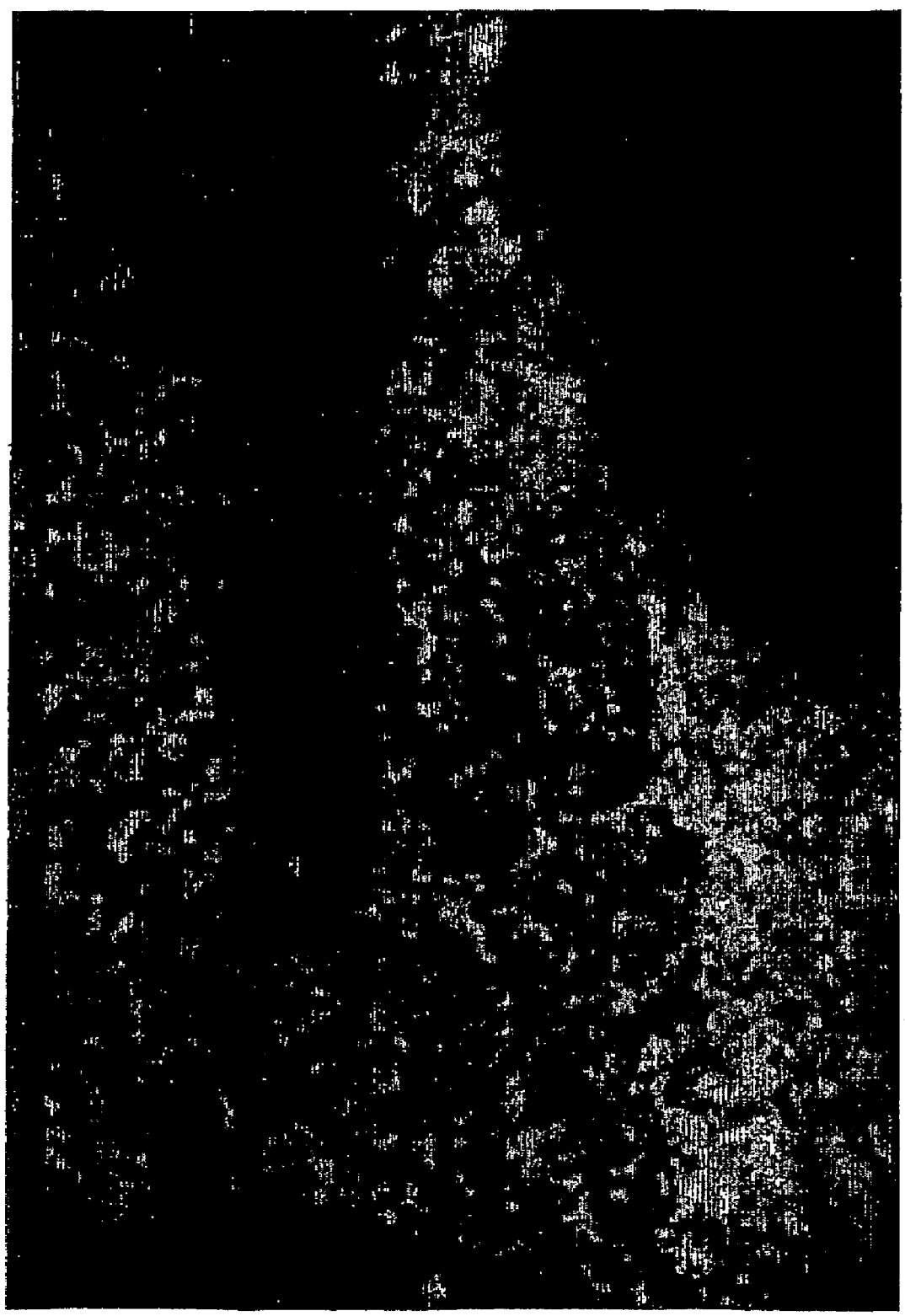
FIG. 3: Imaging of tumor cell death in murine Ly-lymphoma in vivo by Re-NST904 (NST904 attached to oxo-rhenium)

FIG. 3: Imaging of Tumor Cell Death in Murine Ly-Lymphoma In Vivo by Re-NST904 (NST904 Attached to oxo-rhenium):

Mice bearing Ly-lymphoma were treated with chemotherapy (Taxol 20 mg/Kg; one dose), and then injected intravenously with Re-NST904. Animals were sacrificed two hours later, and the tumor was removed and subjected to fluorescent histopathological assessment, to identify binding of Re-NST904. Shown is a fluorescent microscopic image of the tumor. Substantial selective uptake of Re-NST904 by the apoptotic tumor cells is demonstrated. By contrast, viable tumor cells did not manifest such uptake, and therefore remained dark.

Figure 4:
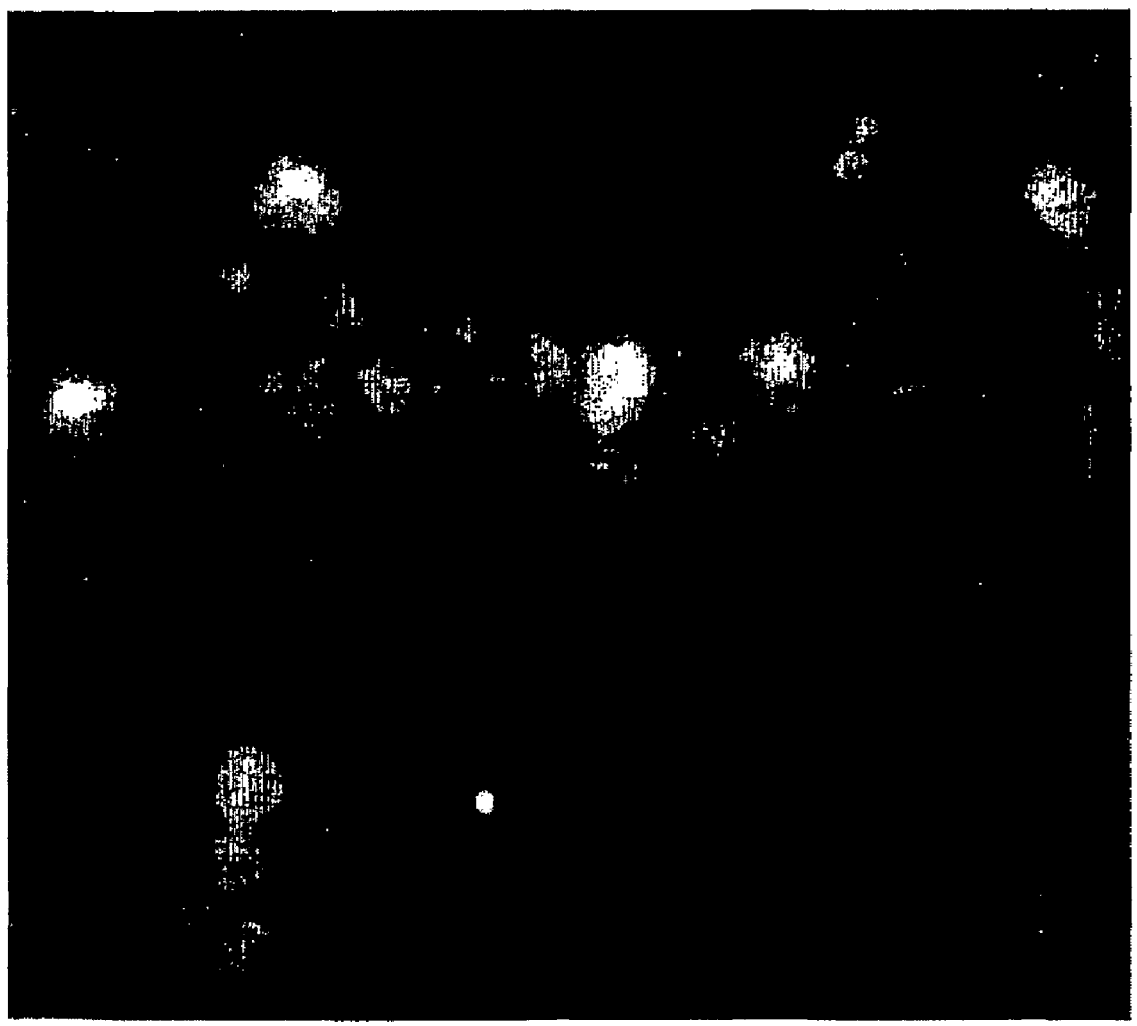
FIG. 4: Imaging of tumor cell death B16 melanoma ii: vivo by NST920B.

FIG. 4: Imaging of Tumor Cell Death B16 Melanoma In Vivo by NST920B:

Mice bearing B16-melanoma were treated with chemotherapy (BiCNU 35 mg/Kg, one dose), and then injected intravenously with NST920B. Animals were sacrificed two hours later, and the tumor was removed and subjected to fluorescent histopathological assessment, to identify binding of NST920B. Shown is fluorescent microscopic image of a section of the tumor. Uptake of NST920B into apoptotic cells is demonstrated. By contrast, viable, non-apoptotic tumor cells did not manifest such uptake, and thus remained dark.

EXAMPLES

Example 1

Synthesis of Thiol-Protected NST904 (Scheme 1)

4-Methoxybenzyl chloride (15.6 g) was reacted with 2-aminoethanethiol (7.7 g) in methanol and sodium methoxide, to afford of 2-(4-methoxybezyl-sulfanyl)-ethylamine (1) (18.8 g). One half of this material was taken in dichloromethane (cooling bath 0° C.). Chloroacetyl chloride in the same solvent, was added slowly with stirring, followed by an equivalent of triethyl amine to produce 2-chloro N-[2-(4-methoxybenzyl-sulfanyl)-ethyl]acetamide (2) in a 94% yield. Compound 2 was reacted with an equivalent amount of 1 in refluxing acetonitrile for 6 hrs to provide N-[-2-(4-methoxy-benzylsulfanyl)-ethyl]-2-[2-(4-methoxy-benzyl-sulfanyl)-ethylamino]-acetamide (3) (40.4 g). Compound 3 was reduced with lithium aluminium hydride (LAH) to yield 4 in 85%.

To a cold solution of anhydrous methanol was added dropwise 10 equivalents of thionyl chloride so as to maintain the internal temperature below 10° C. Reaction mixture was further stirred for 1 hour and treated with 10 g (L)-4-bromo-2-aminobutyric (5). The reaction was slowly warmed to room temperature (RT) over 1 hour and stirred at 40° C. overnight. Volatiles were removed under reduced pressure to dryness, and residue triturated with dichloromethane (DCM) to afford an off white solid (12 g) (6). That solid was dissolved in tetrahydrofuran (THF), treated with 3 eq. diisopropyl ethyl amine (DIPEA) followed by dibutyl oxycarbonyl anhydride (Boc$_2$O). The reaction was stirred at RT for 6 hours. The reaction mixture was diluted with ethyl acetate (100 mL) and the combined organics washed with saturated ammonium chloride (100 mL), brine (100 mL) and dried over sodium sulfate and filtered. The filtrate was concentrated to dryness to afford 11 g of butyloxycarbonyl-2-amino-4-bromobutyric acid methyl ester (7) as a thick oil which slowly crystallized.

Compound 7 was taken up in acetone (10 volumes) and treated with 5 equivalents of sodium iodide. The resulting yellowish solution was refluxed overnight. The reaction was then concentrated to dryness, the residue dissolved in water (150 mL) and extracted with DCM (150 mL). The organic layer was collected, washed with brine, dried and concentrated to dryness to provide 8 g of 8 as a pale oil, purity of 94% (HPLC).

1.3 g of diamine 4 were treated with 2.4 g of iodide 8 in acetonitrile with DIPEA (3 eq) as the base. The reaction was then stirred at 70° C. for 5 hours followed by further stirring at the same temperature overnight. After flash chromatography, Butyl oxycarbonyl-2-amino-4-{(2-{(butyl oxycarbonyl 3-amino-3-methoxycarbonyl-propyl)-[2-(4-methoxy-benzylsulfanyl)-ethyl]-amino}-ethyl)-[2-(4-methoxy-benzylsulfanyl)-ethyl]-amino}-butyric acid methyl ester (9) was obtained (40% yield).

Treatment of 9 (0.9 g) with 10 equivalents of 4M HCl/dioxane solution overnight afforded the dihydrochloride salt 10 in excellent purity and good yield. 5-Dimethylamino-1-naphthalenesulfonyl (dansyl) linkage was achieved by reacting 10 with dansyl chloride and DIPEA to provide 0.9 g of 11 with a purity of >98% after column chromatography. Hydrolysis of the esters was carried in a mixture of dioxane/water (2:1) overnight to provide >95% conversion of the di-ester to 2-Amino-4-{(2-{(3-amino-3-carboxy-propyl)-[2-(4-methoxy-benzylsulfanyl)-ethyl]-amino}-ethyl)-[2-(4-methoxy-benzylsulfanyl)-ethyl]-amin o}-butyric acid (thiol-protected NST904).

At this point the reaction mixture was of a milky suspension and the mixture was diluted with water (10 mL) and the organic solvent removed in vacuo. The milky aqueous layer was then covered with ethyl acetate and acidified to pH 3.0 with 2.0 M HCl. The organic layer was collected, dried and concentrated to dryness to afford an off-white solid of thiol-protected NST904 (1.3 g) which was practically pure. $^1$H NMR (300 MHz, CDCl$_3$) δ 8.87 (d, J=8.87 Hz, 2H), 8.70 (d, J=8.56 Hz, 2H), 8.40 (d, J=7.31 Hz, 2H), 7.98 (d, J=7.63 Hz, 2H), 7.81 (m, 4H), 7.30 (d, J=8.58 Hz, 2H) 6.87 (d, J=8.62 Hz, 2H), 4.05 (dd, J=3.91 Hz, J=4.02 Hz, 2H), 3.58 (bs, 4H), 3.3(, s, 12H), 3.29 (m, 10H), 2.77 (m, 4H), 2.23 (m, 2H), 2.02 (m, 2H). Melting range (DSC) MS(ESI) calcd 1088, found 1089 (M+1). IR (KBr), 3442.86, 2950.0, 1729.97, 1612.46, 1516.32, 1462.91, 1331.16, 1252.82, 1145.99 cm$^{-1}$. HPLC Hypersil BDS, C18 4.5×150 mm, 5μ. Solvent A: H$_2$O/0.1% TFA, solvent B Acetonitrile/0.1% TFA; gradient of 30% B to 100% B over 17.0 min, flow rate 1.0 mL/min, detector @ 254 nm, Rt 10.318 (94.0%).

Scheme 1

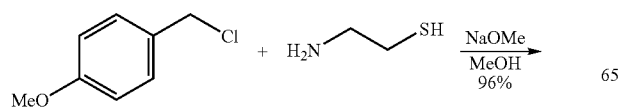

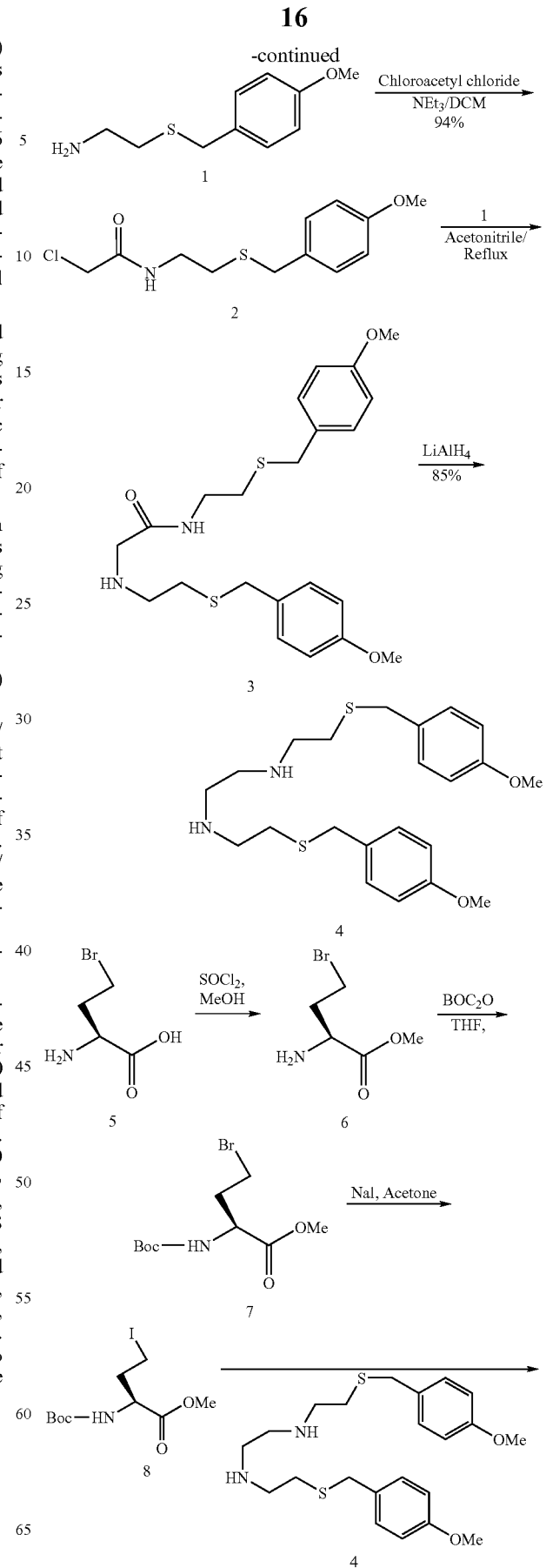

-continued

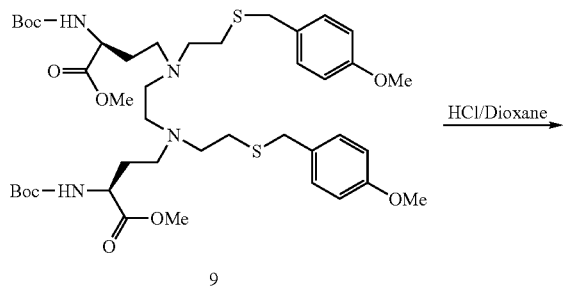

9

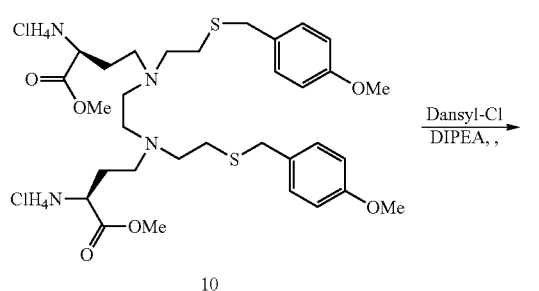

10

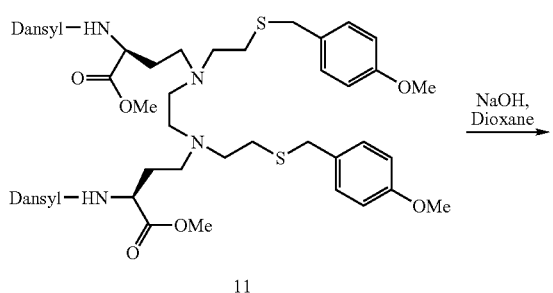

11

-continued

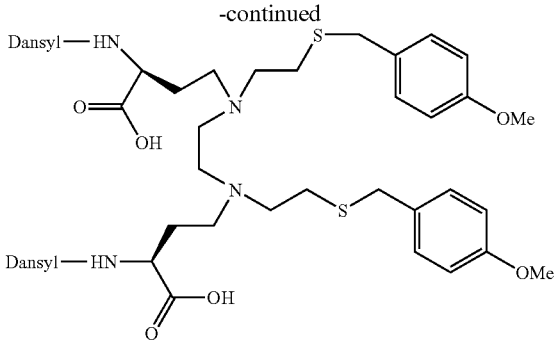

NST904-thiol protected

Example 2

Attachment of Oxo-Rhenium-NST904 Complex (Re-NST904; Scheme 2)

Deprotection—One equivalent of p-methoxybenzyl-protected NST-904 (12) was dissolved in 3 ml TFA ($N_2$ atmosphere). 50 ml of anisole were added followed by addition of 4 equivalents of mercuric acetate. After 1.5 Hrs., TFA was removed, and the solid residue triturated in ether, washed twice with fresh ether and dried. The residue was suspended in methanol and a stream of $H_2S$ was passed trough solution for 10 min. Mixture was filtered through a pad of celite. Methanol was evaporated and residue dried at the pump yielding a lo yellowish-green solid. ESI-MS m/z-849.6.

Complexation ($SnCl_2/NaReO_4$)—Residue obtained from deprotection was dissolved in methanol and approximately same volume of water was added. Two stock solutions were prepared. a—2:1 sodium glucoheptonate: $SnCl_2$, b—$NaReO_4$ in 0.1M HCl. Volume corresponding to 1.3 equivalents of a and b was added to the de-protected NST-904 solution. Then, the mixture was heated overnight to reflux to afford Re-NST904. Solvents were evaporated and residue extracted with acetonitrile. After evaporation, ESI-MS m/z=1049 accompanied by the Sn complex (m/z=965).

The material was purified by semi preparative HPLC.

Scheme 2

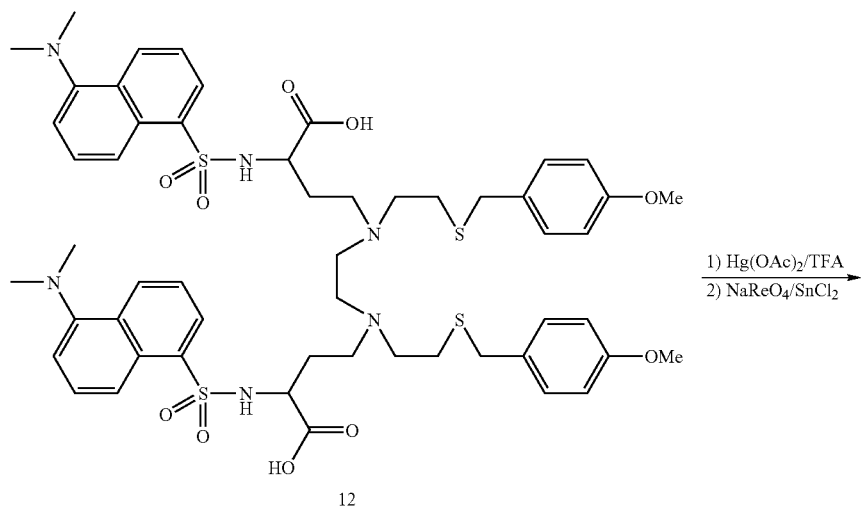

12

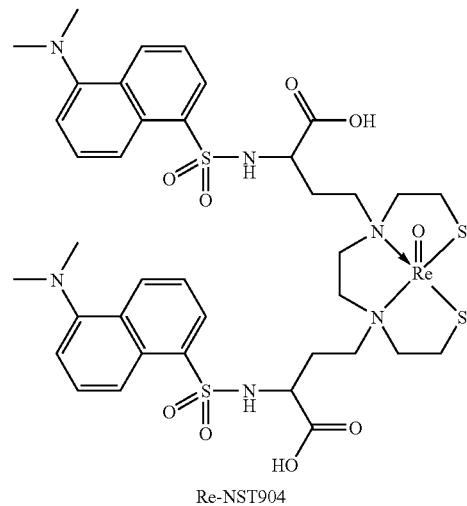

Re-NST904

Example 3

Synthesis of NST912 (Scheme 3)

Compound 8 (4.4 g) was reacted with 4-amino-1-butanol to afford 1.0 g of 4-[(4-Hydroxy-butyl)-(3-methoxycarbonyl-3-t butyloxycarbonylamino-propyl)-amino]-2-t butyloxycaonylamino-butyric acid methyl ester 12. The Boc groups were removed in the usual manner (HCl/Dioxane) yielding 13, and the amine functions were dansylated as specified in Example 1 to yield 14. In order to remove the ester groups 8 equivalents of KOH were added to 14 and the reaction was stirred for 39 hours yielding NST912 in 81% yield—$^1$H NMR (300 MHz, CDCl$_3$) δ 8.53 (d, J=8.4 Hz, 2H), 8.35 (d, J=8.4 Hz, 2H), 8.23 (d, J=7.2 Hz, 2H), 7.59 (t, J=8.1 Hz, 2H), 7.56 (t, J=7.5, 2H), 7.24 (d, J=7.5 Hz, 2H), 3.80-3.70 (m, 2H), 3.55-3.45 (m, 2H), 2.85 (s, 12H), 2.83-2.60 (m, 5H), 2.05-1.80 (m, 5H), 1.55-1.35 (m, 4H). MS for C$_{36}$H$_{47}$N$_5$O$_9$S$_2$ calcd 757, found 758 (M+1).

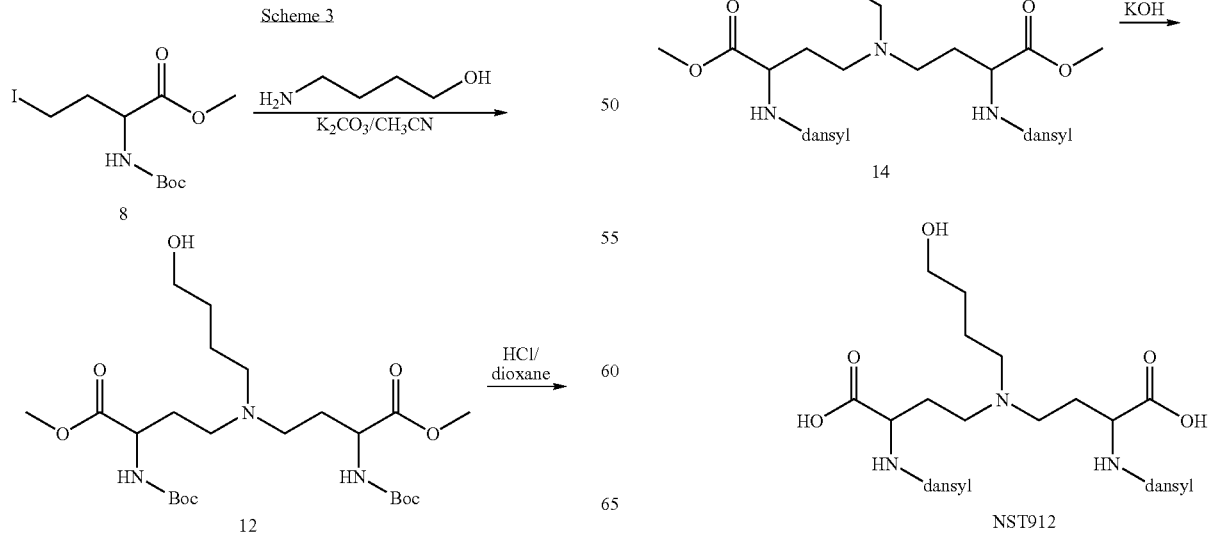

Scheme 3

Example 4

Selective Binding of NST912 to Apoptotic Cells; Flow-Cytometric Analysis

Human adult T-cell leukemia (Jurkat cells) were grown in RPMI 1640 medium supplemented with 2 mM of L-glutamine; 100 units/ml of penicillin; 100 µg/ml of streptomycin; 12.5 units/ml of nystatin; 1 mM sodium pyruvate, 1 mM HEPES and 10% fetal calf serum (FCS). Cells were grown in suspension in vertical flasks and seeded at a density of $5 \times 10^6$ in 10 ml medium. To induce apoptosis, $1 \times 10^6$ cells/ml were treated with IgM anti-Fas antibody at a concentration of 0.1 µg/ml for 120-180 min. Cells were harvested followed by centrifugation at 1600 RPM for 5 min.

The cells were then subjected to analysis by flow cytometry (FACS) using Beckton-Dickinson cell sorter and CellQuest software. Excitation was at 356 nm and emission was measured at 530 nm. As shown in the FACS histogram in FIG. 1, non-treated cells manifested low levels of fluorescence values upon addition of NST912 (solid line). Apoptotic cells shifted to a distinct peak of higher fluorescence levels (dashed line), manifesting selective uptake of NST912 by theses cells. NST912 can therefore act, through its detection of PNOM, as a potent agent to mark and distinguish between apoptotic and non-apoptotic cells.

Example 5

Detection of Chemotherapy-Induced Apoptosis of Mouse Small Intestine Epithelial Cells In Vivo by NST912

Gastrointestinal damage is often observed during administration of anti-cancer therapy. In particular, the small intestine crypts manifest apoptosis of epithelial cells as an early response to chemotherapy and irradiation (Keefe, D. M. K., et al, 2000). Detection of chemotherapy-induced, small intestine epithelial apoptosis by NST912 in vivo was therefore examined.

Twelve-week old Balb/c mice were treated intravenously with a single dose of a combination of Taxol (27 mg/kg) and cyclophosphamide (300 mg/kg). After 24 hours, all animals were injected intravenously with of NST912 (2 mg per animal). Two hours later, animals were sacrificed, small intestine was removed and cryo-sections were prepared for fluorescent microscopy.

Strong, selective uptake of NST912 by apoptotic cells was detected in the small intestinal crypts of the chemotherapy-treated mice (FIG. 2). By contrast, no significant uptake of NST912 was observed in non-apoptotic cells in the crypts of chemotherapy-treated mice (FIG. 2), or in tissues obtained from animals not treated with chemotherapy. This exemplifies the potential usefulness of the compounds of the invention as a tool for an early and sensitive monitoring of this adverse effect of chemotherapy, allowing its detection even after a single dose of anti-cancer treatment.

Example 6

Imaging of Tumor Cell Death in Murine Ly-Lymphoma In Vivo by the Compounds of the Invention Lymphoma cells (from a chemically-induced LY-R clone) were obtained from ATCC(CRL-1722), and maintained by subsequent passages in mice. For 5 induction of tumors, $5 \times 10^5$ cells in a volume of 100 µl were injected subcutaneously into the thigh of 8 week-old male DBA/2 mice (Harlan laboratories, UK). After 10 days, when tumor diameter reached the size of 5-7 mm, mice were subjected to chemotherapy treatment (Taxol, intra-peritoneal injection at a dose of 20 mg/Kg). Twenty-four hours later, a compound of the invention, selected from Re-NST904 (NST904 in complex with oxo-rhenium), NST920B, NST920, and NST930 was administered intravenously (1-3 mg per animal). Mice were sacrificed two hours later, tumors were removed, frozen in liquid nitrogen, and subjected to cryosections. Tissue was subjected to fluorescent microscopy (excitation wavelength of 360 nm, emission at 530 nm), using an Olympus fluorescent microscope (model IX70).

In all the above compounds tested, extensive binding of the compound to apoptotic tumor cells was observed, while viable, non-apoptotic tumor cells remained unstained. Taxol induced a marked increase in the apoptotic load within the tumor, and this was well-reflected by a marked augmentation in the number of cells manifesting uptake of the compounds of the invention and the intensity of staining. FIG. 3 is a representative image of said findings, demonstrating fluorescent microscopy of a tumor from a taxol-treated mouse, following intravenous administration of Re-NST904. Multiple foci of cells, manifesting uptake of Re-NST904 appeared within the tumor tissue, indicative of a massive apoptotic process induced by chemotherapeutic agent. The identity of the stained cells as apoptotic cells was confirmed by histopathological assessment of parallel sections by hemotoxilin and eosin (H&E), as well as by the TUNEL (terminal deoxynucleotidyl transferase mediated dUTP nick end-labeling) staining.

Example 7

Imaging of Tumor Cell Death B16 Melanoma In Vivo by the Compounds of the Invention Melanoma tumors were induced in c57/black mice by subcutaneous injection of B16-F10 cell line (ATCC CRL-6475). The cell line was maintained in culture in Dulbecco's modified Eagle's medium (DMEM), supplemented with 4 mM of L-glutamine; 100 units/ml of penicillin; 100 µg/ml of streptomycin; 12.5 units/ml of nystatin and 10% of fetal calf serum (FCS). For tumor induction, $10^5$ cells in a volume of 100 µl were injected intraperitoneally (i.p.) to 8 week-old male mice. 15 days later, when tumor diameter reached 5-6 mm, the mice were treated with chemotherapy (BiCNU, 1,3-bis(2-chloroethyl)-1-nitrosourea, at a single dose of 35 mg/Kg). Twenty-four hours after chemotherapy, the mice were injected intravenously with the compounds of the invention NST920B, NST930 and Re-NST904 (1-3 mg/animal). Two hours later, tumors were removed, frozen in liquid nitrogen, and subjected to cryosection. Evaluation of fluorescent signal was performed using fluorescent microscope.

FIG. 4 is a representative image, showing selective uptake of NST920B into apoptotic cells within the tumor. By contrast, non-apoptotic tumor cells did not manifest such uptake and remained unstained. As described above in Example 6, the identity of said cells, manifesting uptake of NST920B as apoptotic cells was confirmed by histopathological H&E staining, and also by the TUNEL staining, performed to detect the characteristic apoptotic DNA cleavage. Similar results were obtained also for the other compounds tested, i.e., NST930 and Re-NST904.

The invention claimed is:

1. A diagnostic agent comprising a compound represented by the structure set forth in formula (II):

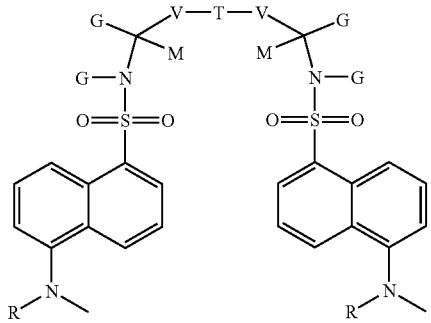

and pharmaceutically acceptable salts, hydrates, solvates and metal chelates of the compound of the formula II;
wherein G groups may be the same or different and are selected independently from hydrogen, —(CH2)$_m$(COOH) and COOH such that said compound of formula II contains one or two carboxyl groups, wherein m is an integer of 1,2 or 3;
V groups are independently absent or —(CH$_2$)$_k$—; k being 1 or 2;
M groups are independently absent or selected from the group consisting of hydrogen, alkyl-amide, hydroxyalkyl and fluoroalkyl, wherein said alkyl has 1, 2 or 3 carbon atoms; and
T is —O—, —S—, —NH—, —N(B)—, —Q—, and —N(B'—Q)—, —N(B'—OH)—, -and —N(B'—F)— wherein B is an optionally substituted alkyl of 1, 2, 3, 4, 5 or 6 carbon atoms and B' is an optionally substituted alkylene of 1 2, 3, 4, 5 or 6 carbon atoms;
Q is a marker for imaging and a metal chelate; said marker for imaging being selected from the group consisting of a fluorescent label, a radio-label, a marker for X-ray, a marker for MRI, or a marker for PET scan; and
R is independently selected from the group consisting of hydrogen, linear or branched alkyl of 1, 2, 3 or 4 carbon atoms, or the group (CH$_2$)$_m$CH(NH$_2$)COOH, wherein m is an integer of 0, 1, 2, 3 or 4;
and a metal.

2. A method, for the detection of cells undergoing apoptosis, comprising the steps of:
(i) administering a diagnostic agent according to claim 1; and
(ii) imaging a patient, so as to identify the presence of cells undergoing apoptosis.

3. A method, for the detection of procoagulant particles, selected from activated platelets, platelet-derived microparticles, and apoptotic bodies, comprising the steps of:
(i) administering a diagnostic agent according to claim 1; and
(ii) imaging a patient, so as to identify the presence of the procoagulant particles, selected from activated platelets, platelet-derived microparticles, and apoptotic bodies.

4. A method, for the detection of a blood clot, comprising the steps of:
(i) administering a diagnostic agent according to claim 1; and
(ii) imaging a patient, so as to identify the presence of the blood clot.

5. A method, for the detection of activated inflammatory cells, selected from activated white blood cells and activated tissue macrophages, comprising the steps of:
(i) administering a diagnostic agent according to claim 1; and
(ii) imaging a patient, so as to identify the presence of the activated inflammatory cells, selected from activated white blood cells and activated tissue macrophages.

6. A method, for detection of cell death within a tumor or for detection of metastases of a tumor, comprising the steps of:
(i) administering a diagnostic agent according to claim 1; and
(ii) imaging a patient, so as to identify the presence of the cell death within a tumor or for detection of metastases of a tumor.

7. A method for the detection of a cell having a perturbed membrane (PM cell) in a cell sample, the method comprising:
(i) contacting the cell sample with a an agent comprising a compound represented by the structure set forth in formula (II):

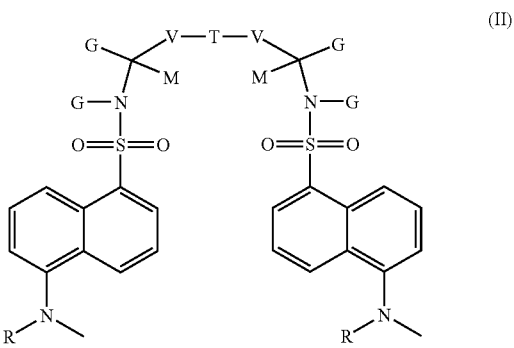

and pharmaceutically acceptable salts, hydrates, solvates and metal chelates of the compound of the formula II;
wherein G groups may be the same or different and are selected independently from hydrogen, —(CH2)$_m$(COOH) and COOH such that said compound of formula II contains one or two carboxyl groups, wherein m is an integer of 1,2 or 3;
V groups are independently absent or —(CH$_2$)$_k$—; k being 1 or 2;
M groups are independently absent or selected from the group consisting of hydrogen, alkyl-amide, hydroxyalkyl and fluoroalkyl, wherein said alkyl has 1, 2 or 3 carbon atoms; and
T is —O—, —S—, —NH—, —N(B)—, -Q-, and —N(B'-Q)- , —N(B'—OH)—, -and —N(B'—F)— wherein B is an optionally substituted alkyl of 1, 2, 3, 4, 5 or 6 carbon atoms and B' is an optionally substituted alkylene of 1, 2, 3, 4, 5 or 6 carbon atoms;
Q is a marker for imaging and a metal chelate; said marker for imaging being selected from the group consisting of a fluorescent label, a radio-label, a marker for X-ray, a marker for MRI, or a marker for PET scan; and
R is independently selected from the group consisting of hydrogen, linear or branched alkyl of 1, 2, 3 or 4 carbon atoms, or the group $(CH_2)_m CH(NH_2)COOH$, wherein m is an integer of 0, 1, 2, 3 or 4;

(ii) detecting the amount of agent bound to said cell in said sample;

(iii) comparing the amount of agent bound to said cell in said sample with an amount of the agent bound to a control cell, said control cell being a cell maintaining its normal membrane organization;

wherein if more of the agent is bound to said cell in said sample than the amount of agent bound to said control cell, said cell in said sample being detected as a PM cell.

8. A compound, represented by the structure set forth in formula (II):

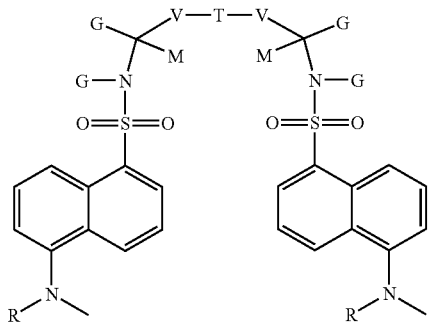

and pharmaceutically acceptable salts, hydrates, solvates and metal chelates of the compound of the formula II;

wherein G groups may be the same or different and are selected independently from hydrogen, $-(CH2)_m(COOH)$ and COOH such that said compound of formula II contains one or two carboxyl groups, wherein m is an integer of 1, 2 or 3;

V groups are independently absent or $-(CH_2)_k-$; k being 1 or 2;

M groups are independently absent or selected from the group consisting of hydrogen, alkyl-amide, hydroxyalkyl and fluoroalkyl, wherein said alkyl has 1, 2 or 3 carbon atoms; and T is $-O-$, $-S-$, $-NH-$, $-N(B)-$, -Q-, and $-N(B'-Q)-$, $-N(B'-OH)-$, -and $-N(B'-F)-$ wherein B is an optionally substituted alkyl of 1 2, 3. 4, 5 or 6 carbon atoms and B' is an optionally substituted alkylene of 1, 2, 3, 4, 5 or 6 carbon atoms;

Q is a marker for imaging and a metal chelate: said marker for imaging being selected from the group consisting of a fluorescent label, a radio-label, a marker for X-ray, a marker for MRI, or a marker for PET scan; and R is independently selected from the group consisting of hydrogen, linear or branched alkyl of 1, 2, 3 or 4 carbon atoms, or the group $(CH_2)_m CH(NH_2)COOH$, wherein m is an integer of 0, 1, 2, 3 or 4;

comprising or being linked to a marker for imaging, wherein said marker for imaging is selected from a group consisting of Tc, Tc=O, In, Cu, Ga, Xe, Tl, Re and Re=O, $^{123}I$, $^{131}I$, Gd(III), Fe(III), $Fe_2O_3$, $Fe_3O_4$, Mn(II) $^{18}F$, $^{15}O$, $^{18}O$, $^{11}C$, $^{13}C$, $^{124}I$, $^{13}N$, $^{75}Br$, Tc-99m or In-111.

9. A compound represented by the structure set forth in formula (III):

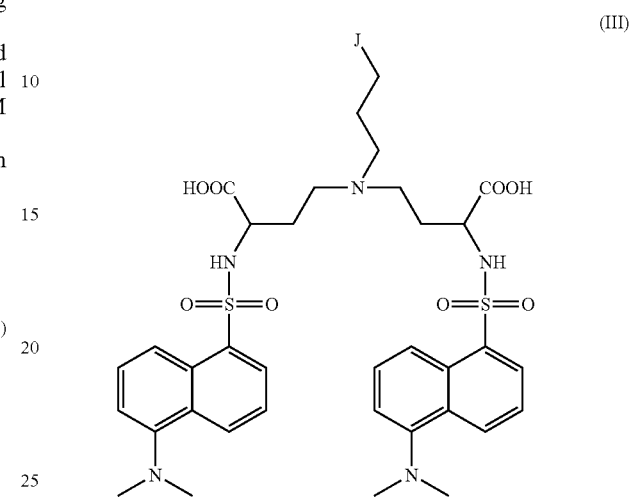

wherein J is selected from the group consisting of hydrogen, $-OH$, and -Q; wherein said Q is selected from the group consisting of an $N_2S_2$ chelator and $-F$; and pharmaceutically acceptable salts, hydrates, solvates and metal chelates of the compound of the formula III.

10. The compound of claim 9 represented by the structure set forth in formula (IV):

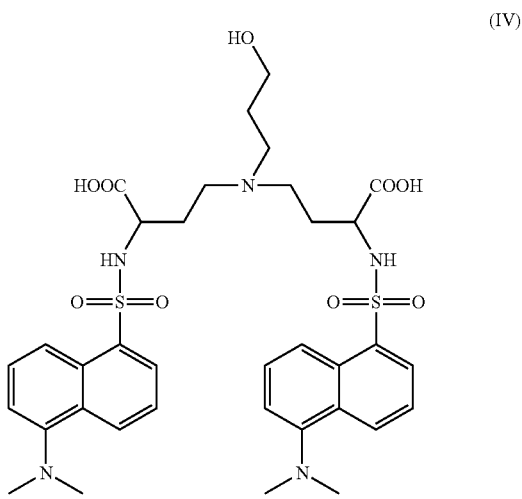

and pharmaceutically acceptable salts, hydrates, solvates and metal chelates of the compound of the formula IV.

11. The compound of claim 9 represented by the structure set forth in formula V:

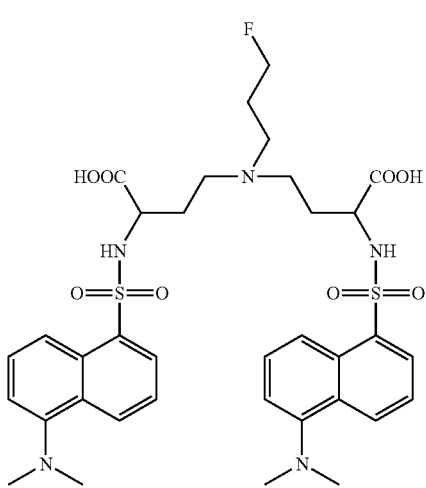

(V)

and pharmaceutically acceptable salts, hydrates, solvates and metal chelates of the compound of formula (V).

12. The compound of claim 9 represented by the structure set forth in formula VI:

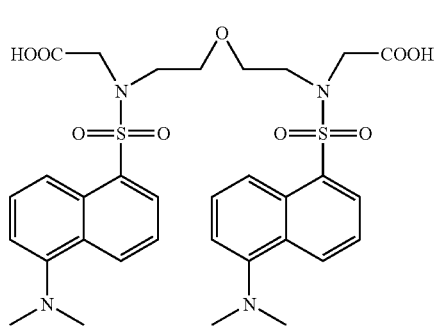

(VI)

and pharmaceutically acceptable salts, hydrates, solvates and metal chelates of the compound of formula (VI).

13. A compound represented by the structure set forth in formula VII:

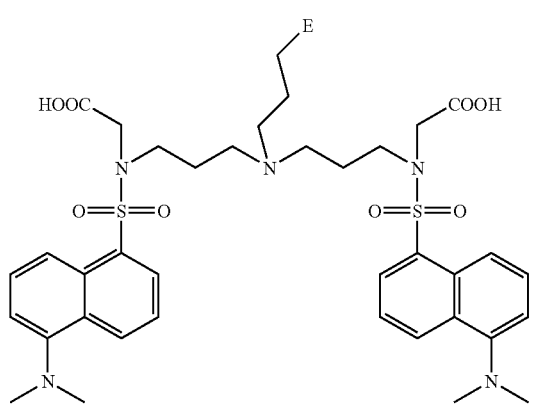

(VII)

wherein E is selected from —OH, —F, —CH$_3$ and Q; wherein said Q is selected from an N$_2$S$_2$ chelator and —F;

and pharmaceutically acceptable salts, hydrates, solvates and metal chelates of the compound of formula (VII).

14. The compound of claim 13 represented by the structure set forth in formula VIII:

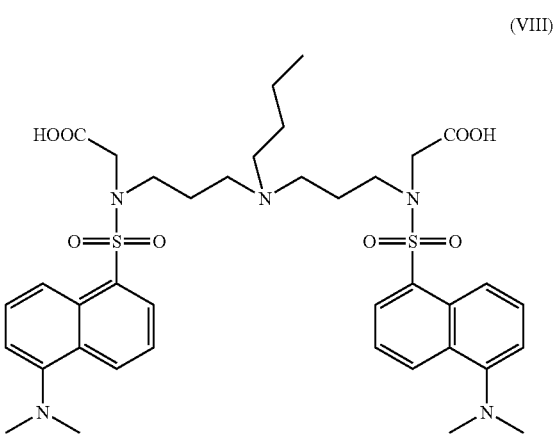

(VIII)

and pharmaceutically acceptable salts, hydrates, solvates and metal chelates of the compound of formula (VIII).

15. The compound of claim 13 represented by the structure set forth in formula IX:

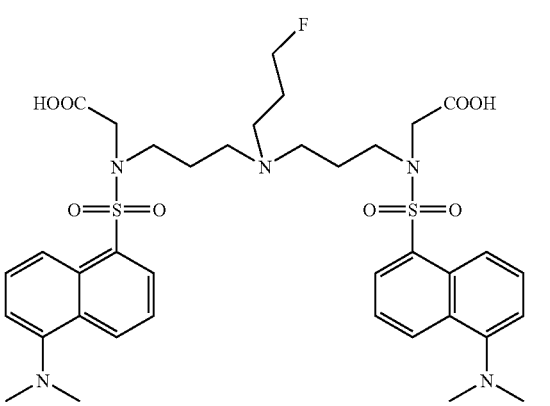

(IX)

and pharmaceutically acceptable salts, hydrates, solvates and metal chelates of the compound of formula (IX).

16. A compound represented by the structure set forth in formula X:

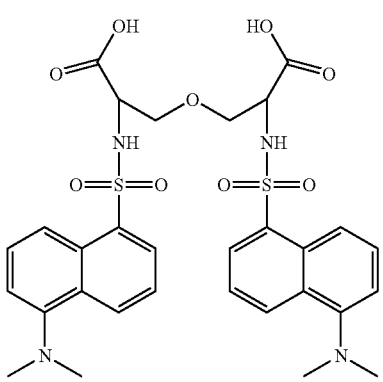
(X)

and pharmaceutically acceptable salts, hydrates, solvates and metal chelates of the compound of formula (X).

17. A compound represented by the structure set forth in formula XI:

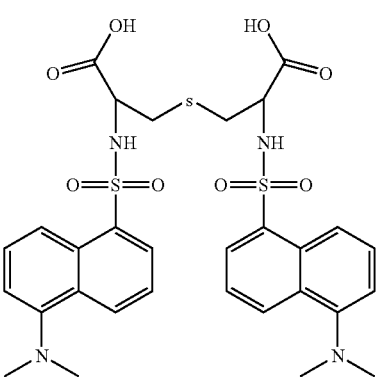
(XI)

and pharmaceutically acceptable salts, hydrates, sot yates and metal chelates of the compound of formula (XI).

18. A compound represented by the structure set forth in formula XII:

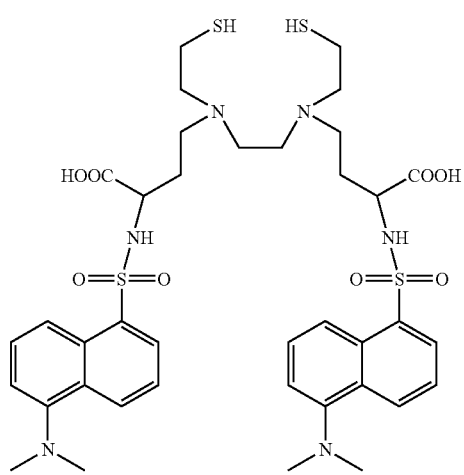
(XII)

and pharmaceutically acceptable salts, hydrates, solvates and metal chelates of the compound of the formula XII.

19. A compound represented by the structure set forth in formula (II):

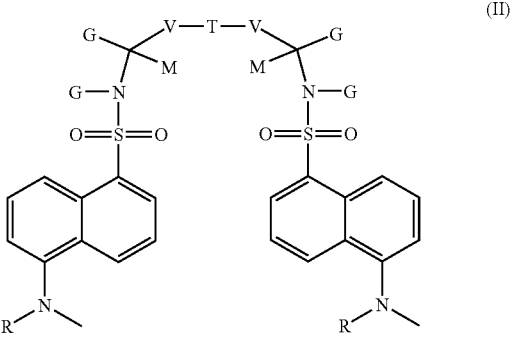
(II)

and pharmaceutically acceptable salts, hydrates, solvates and metal chelates of the compound of the formula II;

wherein G groups may be the same or different and are selected independently from hydrogen, $—(CH2)_m$ (COOH) and COOH such that said compound of formula II contains one or two carboxyl groups, wherein m is an integer of 1,2 or 3:

V groups are independently absent or $—(CH_2)_k—$; k being 1 or 2;

M groups are independently absent or selected from the group consisting of hydrogen, alkyl-amide, hydroxyalkyl and fluoroalkyl, wherein said alkyl has 1, 2 or 3 carbon atoms; and T is —O—, —NH—, —N(B)—, -Q-, and —N(B'-Q)—, —N(B'—OH)—, -and —N(B'—F)—wherein B is an optionally substituted alkyl of 1, 2, 3, 4, 5 or 6 carbon atoms and B' is an optionally substituted alkylene of 1, 2, 3, 4, 5 or 6 carbon atoms;

Q is a marker for imaging and a metal chelate; said marker for imaging being selected from the group consisting of a fluorescent label, a radio-label, a marker for X-ray, a marker for MRI, or a marker for PET scan; and R is independently selected from the group consisting of hydrogen, linear or branched alkyl of 1, 2, 3 or 4 carbon atoms, or the group $(CH_2)_m CH(NH_2)COOH$, wherein m is an integer of 0, 1, 2, 3 or 4;

wherein the chelated metal is selected from the group consisting of Technetium, oxo-technetium, Rhenium and oxo-rhenium radioisotopes.

* * * * *

UNITED STATES PATENT AND TRADEMARK OFFICE
CERTIFICATE OF CORRECTION

PATENT NO.        : 7,378,079 B2                                    Page 1 of 1
APPLICATION NO.  : 10/516616
DATED             : May 27, 2008
INVENTOR(S)       : Ziv et al.

It is certified that error appears in the above-identified patent and that said Letters Patent is hereby corrected as shown below:

Claim 1, Column 23, Line 38,
Please delete "of 1 2,3, 4, 5, or 6 carbon atoms;"
and
replace with
-- of 1, 2, 3, 4, 5, or 6 carbon atoms; --

Claim 7, Column 24, Line 25,
Please delete "with a an agent"
and
replace with
-- with an agent --

Claim 8, Column 25, Line 51,
Please delete "of 1 2, 3. 4, 5 or 6"
and
replace with
-- of 1, 2, 3, 4, 5, or 6 --

Claim 17, Column 29, Line 40,
Please delete "hydrates, sot yates"
and
replace with
-- hydrates, solvates --

Signed and Sealed this

Second Day of September, 2008

JON W. DUDAS
*Director of the United States Patent and Trademark Office*